(12) United States Patent
Ibrahim

(10) Patent No.: US 10,004,676 B2
(45) Date of Patent: Jun. 26, 2018

(54) **DENTIFRICE COMPOSITIONS CONTAINING EXTRACTS OF *NIGELLA SATIVA* AND RELATED METHODS**

(71) Applicant: Health and Natural Beauty USA Corp., New Brunswick, NJ (US)

(72) Inventor: Sayed Ibrahim, New Brunswick, NJ (US)

(73) Assignee: Health and Natural Beauty USA Corp., New Brunswick, NJ (US)

( * ) Notice: Subject to any disclaimer, the term of this patent is extended or adjusted under 35 U.S.C. 154(b) by 21 days.

(21) Appl. No.: 14/250,841

(22) Filed: Apr. 11, 2014

(65) Prior Publication Data

US 2014/0308219 A1    Oct. 16, 2014

Related U.S. Application Data

(60) Provisional application No. 61/811,469, filed on Apr. 12, 2013.

(51) Int. Cl.
| *A61K 8/97* | (2017.01) |
| *A61Q 11/00* | (2006.01) |
| *A61K 8/27* | (2006.01) |
| *A61K 36/71* | (2006.01) |

(52) U.S. Cl.
CPC ............ *A61K 8/97* (2013.01); *A61K 8/27* (2013.01); *A61K 36/71* (2013.01); *A61Q 11/00* (2013.01)

(58) Field of Classification Search
None
See application file for complete search history.

(56) References Cited

U.S. PATENT DOCUMENTS

| 6,162,447 A * | 12/2000 | Fankhauser ............ A61K 8/068 424/401 |
| 2005/0214393 A1 | 9/2005 | Kandil |
| 2007/0116652 A1 | 5/2007 | Kamath et al. |
| 2007/0148213 A1* | 6/2007 | Ibrahim ............... A61K 8/0208 424/443 |
| 2010/0278991 A1 | 11/2010 | Haught |
| 2013/0034529 A1 | 2/2013 | Alzahrani et al. |

FOREIGN PATENT DOCUMENTS

| JP | 60054312 A | 3/1985 |
| WO | 2011009862 A1 | 1/2011 |
| WO | 2011068811 A1 | 6/2011 |

OTHER PUBLICATIONS

International Search Report on Patentability and the Written Opinion dated Aug. 14, 2014 received in related PCT/US 2014/000716.
XP-002760290, Mintel, http://www.gnpd.com, Jan. 1, 2008.
Extended European Search Report for EP Application No. 14782615.0, dated Jul. 27, 2016.
Saudi Arabia Examination Report for SA Application No. 515360805, dated Jun. 22, 2016.
One Antaki, Seed of Blessing Toothpaste, published on the internet on Nov. 24, 2009.
Omar, Ola Moustafa, Alternative Medicine: Implications on Dentistry, Alternative and Integrative Medicine, vol. 1, Issue 1, 2013.

* cited by examiner

*Primary Examiner* — Terry A McKelvey
*Assistant Examiner* — Catheryne Chen
(74) *Attorney, Agent, or Firm* — Greenberg Traurig, LLP

(57) ABSTRACT

The present invention relates to dentifrice compositions, in particular, toothpaste compositions, containing extracts of *Nigella sativa*, or black seed oil, and methods of preparing and using the same.

1 Claim, No Drawings

DENTIFRICE COMPOSITIONS CONTAINING EXTRACTS OF *NIGELLA SATIVA* AND RELATED METHODS

This claims the benefit of priority of U.S. application 61/811,469, filed Apr. 12, 2013, incorporated herein by reference in its entirety.

FIELD OF THE INVENTION

The present invention relates to dentifrice compositions, in particular, toothpaste compositions, containing extracts of *Nigella sativa*, or black seed oil, and methods of preparing and using the same.

BACKGROUND

Dentifrice compositions are widely used in order to provide oral health. Dentifrices in the form of toothpaste, mouth rinses, chewing gums, edible strips, powders, foams, and the like have been formulated with a wide variety of active materials that provide a number of benefits to the user. Among these benefits are antimicrobial, anti-inflammatory, and antioxidant properties. These properties of dentifrices make them useful therapeutic agents to prevent or treat a number of oral health conditions such as cavities, gingivitis, plaque, tartar, periodontal disease, and the like.

Practicing good oral hygiene is critical in the prevention of tooth decay and periodontal gum disease. Areas that are particularly problematic for cleaning with a toothbrush are near the gum line (beneath the lower teeth and above the upper teeth) and in interproximal (between) tooth surfaces. Some of the bacteria are presented in the form of a clear (almost invisible) sticky film, plaque, which must be mechanically removed by brushing and flossing.

The plaque forms at all ages, both on non-permanent "baby" and on permanent "adult" teeth. It adheres to the surface of teeth, gum tissues, dental restoration, and even to the tongue. Studies have shown that plaque forms very soon, as fast as four hours after removal of the previous portion of residual plaque. When oral hygiene is poor, within about three weeks the presence of the plaque results in occurrence of gingivitis. As noted, with diligent flossing and tooth brushing gingivitis is reversible and the inflammatory conditions usually disappear. In the absence of such oral hygiene, periodontal disease starts progressing. Plaque control is the only effective method of controlling chronic periodontal disease.

People use mechanical devices to control plaque. There are toothbrushes, toothpaste, interdental cleaning aids, oral irrigation devices, etc. However, these techniques have several limitations and the entire tooth surface cannot be cleaned perfectly. Moreover, once the plaque is deposited in considerable quantities, it is difficult to remove it with common mechanical methods.

Numerous toothpastes are represented in the relevant art. For example, U.S. Pat. No. 6,610,277 B2 discloses appetite suppressant toothpaste formulations, which simultaneously [suppress] the user's appetite while promoting intraoral cleanliness. The toothpaste composition includes toothpaste base ingredients and at least one of appetite suppressant and appetite depressant herbs. The toothpaste base ingredients include a combination of known amounts of Vegetable Glycerin; Sorbitol, Hydrated Silica; Purified Water; Xylitol; Carrageenan; Sodium Lauryl Sulfate; and Titanium Dioxide and a flavoring agent. The appetite suppressing and depressing herbs include at least one of *Garcinia Cambogia; Gymnema Sylvestre*; Kola Nut; Citrus Aurantium; Yerba Mate; and *Griffonia Simplicifolia* and comprise a range of substantially 5.5% to substantially 22% by weight of the composition. The appetite suppressing and depressing herbs may further include at least one of Guarana, Green Tea, myrrh, guggul Lipid and black current seed oil. Alternatively, the toothpaste composition may be in the form of a dental cream or mouthspray.

In another example, United States patent application US 20080253976 A1 discloses personal care compositions, including compositions for oral, throat and skin care comprising a blend of naturally occurring flavor or perfume ingredients or essential oils containing such ingredients, wherein the blend provides excellent antimicrobial activity and comprises at least two components, a first acyclic component selected from citral, neral, geranial, geraniol and nerol and a second cyclic-containing component selected from eucalyptol, carvacrol and eugenol. Preferably, the blend comprises 3, 4, 5 or more of the above components. Greater synergy in terms of antimicrobial efficacy may be obtained [when] different components are blended together. The present compositions are effective in killing, suppressing the growth of and/or altering metabolism of microorganisms including those which cause undesirable oral cavity conditions including plaque, caries, calculus, gingivitis, periodontal disease and malodor. Optionally the blend further comprises additional antimicrobial and/or anti-inflammatory components, preferably naturally-occurring as well.

In another example, United States patent application US 20090087501 A1 discloses oral compositions having at least two botanical active ingredients derived from plants. The oral composition also includes an orally acceptable vehicle to deliver an effective amount of the at least two active ingredients in vivo. The botanical active ingredients provide particularly efficacious antimicrobial (antibacterial, antiviral, and/or antifungal), antioxidant, anti-inflammatory, anti-ageing, and/or healing properties to the oral compositions.

In another example, United States patent application US 20090269288 A1 discloses a toothpaste to prevent decay, to prevent and control dental [plaque] and gingivitis, and to suppress growth of wide spectrum of micro organisms that cause periodontal disease, while not exhibiting any harmful particular side effect. It allows absorbing and removing odor components out of the oral cavity for a long period of time, removing stain from the teeth, and polishing them. The toothpaste comprises: Sodium Monofluorophosphate, Glycerin, Water, Calcium Carbonate, Xylitol-70%, Sodium Dodecyl Sulfate, Sodium Saccharin, Sodium Bicarbonate, Sodium Methylparaben, Xanthan Gum (E-415), Cellulose Gum (E-466), Hydrated Silica, Titanium Dioxide (E-171), Peppermint Oil, Commiphora Myrrh Extract, Menthol, Charcoal, Grape Seed Oil, and Extract of Brazilian Acai Berry. Particular amounts of weight units for preferred embodiments are provided, as well as a sample method of preparation the toothpaste.

In another example, United States patent application US 20120244086 A1 discloses [dentifrice compositions] comprising: a combination of extracts comprising an extract from *Zingiber officinale* and a natural extract other than the extract from *Zingiber officinale*; and an orally acceptable carrier.

In another example, United States patent application US 20120244087 A1 discloses [dentifrice compositions] comprising a combination of extracts comprising a mixture of extracts from at least three of *Punica granatum, Myristica fragrans, Zingiber officinale*, and *Zizyphus joazeiro* and a natural extract other than the extract from at least three of

*Punica granatum, Myristica fragrans, Zingiber officinale,* and *Zizyphus joazeiro*; and an orally acceptable carrier, and methods of preparing and using the same.

The compositions disclosed in the above references do not soothe dry mouth, nor moisturize mouth tissues. There remains, therefore, a need to provide dentifrice, and in particular, toothpaste compositions containing natural extracts or plant oils that are capable of moisturizing mouth tissues, can sooth dry mouth, and that also show decreased astringency.

The present invention provides dentifrice, and in particular, toothpaste compositions that contain extracts of *Nigella sativa*, or black seed oil, and methods to manufacture the compositions. It has been found that the compositions of the present invention moisturize mouth tissues, sooth dry mouth and showed decreased astringency.

SUMMARY

In one embodiment, the present invention provides a dentifrice, in particular, a toothpaste composition, formulated with an extract of *Nigella sativa*, and an orally acceptable carrier.

In one embodiment, the dentifrice or toothpaste composition contains at least one humectant.

In one embodiment, the dentifrice or toothpaste composition contains at least one antibacterial agent. In one embodiment, the antibacterial agent is the extract of *Nigella sativa*. In one embodiment, the dentifrice or toothpaste composition contains at least one additional antibacterial agent.

In one embodiment, the dentifrice or toothpaste composition contains at least one agent selected from the group consisting of anticaries agent, anticalculus or tartar control agents, anionic carboxylate polymers, viscosity modifiers, surfactants, flavorants, and pigments.

In one embodiment, the dentifrice or toothpaste composition contains at least one fluoride releasing salt.

In one embodiment, the dentifrice or toothpaste composition contains at least one zinc releasing salt.

In one embodiment, the dentifrice or toothpaste composition contains at least one abrasive material.

DETAILED DESCRIPTION

For clarity of disclosure, and not by way of limitation, the detailed description of the invention is divided into the following subsections that describe or illustrate certain features, embodiments or applications of the present invention.

As used herein, "antibacterial activity" herein means activity as determined by any generally accepted in vitro or in vivo antibacterial assay or test. "Antioxidant activity" as used herein means activity as determined by any generally accepted in vitro or in vivo antioxidant assay or test.

An "oral surface" as used herein encompasses any soft or hard surface within the mouth including surfaces of the tongue, hard and soft palate, buccal mucosa, gums and dental surfaces. A "dental surface" as used herein is a surface of a natural tooth or a hard surface of artificial dentition including a crown, cap, filling, bridge, denture, dental implant and the like. The term "inhibiting" as used herein with respect to a condition such as inflammation in an oral tissue encompasses prevention, suppression, reduction in extent or severity, or amelioration of the condition.

The expression "natural extract" as used herein denotes any extract that is obtained from a natural source, such as a plant, fruit, tree, seed, and the like.

An oral care composition of the present invention can take any form suitable for application to an oral surface. In various illustrative embodiments the composition can be a liquid solution suitable for irrigating, rinsing or spraying; a dentifrice such as a powder, toothpaste or dental gel; a periodontal gel; a liquid suitable for painting a dental surface (e.g., a liquid whitener); a chewing gum; a dissolvable, partially dissolvable or non-dissolvable film or strip or patch (e.g., a whitening strip); a bead (e.g., composition encapsulated in gelatin); a wafer; a wipe or towelette; an implant; a mouthrinse; a foam; dental floss; etc. The composition can contain active and/or carrier ingredients additional to those recited in the present invention.

Classification herein of an ingredient as an active agent or a carrier ingredient is made for clarity and convenience, and no inference should be drawn that a particular ingredient necessarily functions in the composition in accordance with its classification herein. Furthermore, a particular ingredient can serve a plurality of functions, thus disclosure of an ingredient herein as exemplifying one functional class does not exclude the possibility that it can also exemplify another functional class.

Use of Extracts of *Nigella Sativa*, or Oils Obtained from *Nigella Sativa* in the Compositions of the Present Invention In various embodiments, the invention is based in part on the discovery that when components found in extracts of *Nigella sativa*, or oils from *Nigella sativa* are added to dentifrice compositions, the ability of the dentifrice composition to lubricate the mouth tissues and/or treat dry mouth is enhanced. In certain embodiments, when components found in extracts of *Nigella sativa*, or oils from *Nigella sativa* are added to dentifrice compositions, the astringency of the compositions is reduced. Accordingly, the invention provides in various embodiments dentifrice compositions that contain a combination of extracts, including an extract of *Nigella sativa*, or oils from *Nigella sativa*.

*Nigella sativa* (also referred to as black cumin, black seed, or black curcumin) is an annual flowering plant, native to south and southwest Asia. It grows to 20-30 cm (7.9-12 in) tall, with finely divided, linear (but not thread-like) leaves. The flowers are delicate, and usually colored pale blue and white, with five to ten petals. The fruit is a large and inflated capsule composed of three to seven united follicles, each containing numerous seeds. The seed may be used as a spice. *Nigella sativa* has a pungent bitter taste and smell.

*Nigella sativa* is traditionally used in the Indian subcontinent, Arabian countries, and Europe for culinary and medicinal purposes as a natural remedy for a number of illnesses and conditions that include asthma, hypertension, diabetes, inflammation, cough, bronchitis, headache, eczema, fever, dizziness and influenza. Much of the biological activity of the seeds is believed to be due to thymoquinone (TQ), the putative active phytochemical of *Nigella sativa*, a component of the essential oil. TQ is also present in the fixed oil. *Nigella sativa* oil also contains conjugated linoleic (18:2) acid, nigellone (dithymoquinone), melanthin, nigilline, damascenine, and tannins.

As referred to herein, an "extract" suitable for use in the various embodiments of the present invention can be obtained from any part of a plant including the leaf, stem, stalk, cortex (i.e., bark), pulp, seed, flesh, juice, root, flower, or any other suitable part of a plant or other natural source. The term "botanical active ingredient" encompasses extracts, oils or galenical compositions, active compounds, derivatives, synthetic or semi-synthetic equivalents of such natural extracts and/or active compounds contained therein. Thus, in certain aspects, one or more of the active ingredients includes a derivative or synthetic compound similar to the compounds (thus "derived from") from the natural sources, such as natural botanical extracts. It should be noted that certain natural extracts are in lipophilic carriers, such as is the case with essential oils, or where the extract is diluted in an oil carrier. Other extracts may be partially or fully separated from the lipophilic carriers and merely contain the active compounds of the extract and hydrophobic carriers or solvents. The extracts may be in liquid or dried powder forms.

As used herein, "extracting" or "extraction" of a solid or liquid material means contacting the material with an appropriate solvent to remove the substance(s) desired to be extracted from the material. Where the material is solid, it is preferably dried and crushed or ground prior to contacting it with the solvent. Such an extraction may be carried out by conventional means known to one of skill in the art, for example, by using an extraction apparatus, such as a Soxhlet apparatus, which retains the solid material in a holder and allows the solvent to flow through the material; by blending the solvent and material together and then separating the liquid and solid phases or two immiscible liquid phases, such as by filtration or by settling and decanting. In various embodiments, the botanical active ingredients used in oral care compositions are of reproducible, stable quality and have microbiological safety.

*Nigella sativa* extracts may be prepared by any method, provided the extraction process does not render the extract unsuitable for use in the compositions of the present invention.

In one embodiment, *Nigella sativa* extracts suitable for use in the compositions of the present invention are prepared according to the methods described in United States patent application US 20110076346 A1.

In an alternate embodiment, *Nigella sativa* extracts suitable for use in the compositions of the present invention are prepared according to the methods described in United States patent application US 20090087501 A1.

In one embodiment, *Nigella sativa* extracts suitable for use in the compositions of the present invention are obtained from commercial sources.

In one embodiment, the *Nigella sativa* extract used in the compositions of the present invention is the oil extracted from the seeds. The oil may be further refined, to isolate at least one compound selected from the group consisting of thymoquinone, conjugated linoleic (18:2) acid, nigellone (dithymoquinone), melanthin, nigilline, damascenine, and tannins.

In one embodiment, the *Nigella sativa* extract used in the compositions of the present invention is further combined with at least one other plant extract, such as, for example, morniga oil, and morniga extract, or ginger extract.

In one embodiment, the *Nigella sativa* extract used in the compositions of the present invention is further combined with at least one other plant extract disclosed in United States patent application US 20120244086 A1.

In one embodiment, the *Nigella sativa* extract used in the compositions of the present invention is further combined with at least one other plant extract disclosed in United States patent application US 20120244087 A1.

In one embodiment, the *Nigella sativa* extract used in the compositions of the present invention is further combined with at least one other plant extract disclosed in United States patent application US 20080253976 A1.

In one embodiment, the *Nigella sativa* extract used in the compositions of the present invention is further combined with at least one other plant extract disclosed in U.S. Pat. No. 8,246,938 B2.

Formulation of the Compositions of the Present Invention

The individual ingredients that comprise a dentifrice, in particular, a toothpaste composition of the present invention may be combined by any suitable method. Such a method is readily discernable by one of skill in the art. In one embodiment, the compositions of the present invention utilize kosher ingredients. In one embodiment, the compositions of the present invention utilize halal ingredients.

In one embodiment, the individual ingredients that comprise a dentifrice are combined to form a formulation that is used as toothpaste. In one embodiment, the toothpaste formulation is the formulation described in Example 1. In one embodiment, the toothpaste formulation is the formulation described in Example 2. In one embodiment, the toothpaste formulation is the formulation described in Example 3. In one embodiment, the toothpaste formulation is the formulation described in Example 4. In one embodiment, the toothpaste formulation is the formulation described in Example 5. In one embodiment, the toothpaste formulation is the formulation described in Example 6. In one embodiment, the toothpaste formulation is the formulation described in Example 7. In one embodiment, the toothpaste formulation is the formulation described in Example 8. In one embodiment, the toothpaste formulation is the formulation described in Example 9.

In one embodiment, the individual ingredients that comprise a dentifrice are combined to form a formulation that is used as tooth whitening strips. In one embodiment, the tooth whitening strips utilize hydrogen peroxide as a whitening agent. The formulation of the strip and whitening agent is readily selected by one of skill in the art. For example, in one embodiment, the individual ingredients that comprise a dentifrice are combined to form a formulation that is used as tooth whitening strips, comprising an effective amount of a combination of extracts of *Nigella sativa*, or oils obtained from *Nigella sativa*, and the tooth whitening strip disclosed in EP1871337 A1.

In one embodiment, the individual ingredients that comprise a dentifrice are combined to form a spray. In one embodiment, the spray contains 0.01% to 90% by weight of the combination of extracts of *Nigella sativa*, or oils obtained from *Nigella sativa*.

In various embodiments, the compositions are formulated containing at least one humectant, at least one abrasive material, a carrier, and an effective amount of a combination of extracts of *Nigella sativa*, or oils obtained from *Nigella sativa*. In one embodiment, the compositions contain 0.01% to 10% by weight of the combination of extracts of *Nigella sativa*, or oils obtained from *Nigella sativa*, alternatively, 0.01% to 5% by weight of the combination of extracts of *Nigella sativa*, or oils obtained from *Nigella sativa*, alternatively, 0.1% to 2% by weight of the combination of extracts of *Nigella sativa*, or oils obtained from *Nigella sativa*. In various embodiments, the compositions contain 1% to 70% by weight of at least one humectant, and 1% to 70% by weight of at least one abrasive material, in addition to 0.1% to 2% by weight of the combination of extracts of *Nigella sativa*, or oils obtained from *Nigella sativa*.

In various embodiments, the compositions contain an antibacterial agent comprising extracts of *Nigella sativa*, or oils obtained from *Nigella sativa*.

In various embodiments, the compositions contain an anti-inflammatory agent comprising extracts of *Nigella sativa*, or oils obtained from *Nigella sativa*.

In various embodiments, the compositions contain an antioxidant agent comprising extracts of *Nigella sativa*, or oils obtained from *Nigella sativa*.

In various embodiments, the compositions do not include additional antibacterial agents, although their use is optional. In the event additional antibacterial agents are used, the compositions may further comprise an antibacterial agent selected from the group consisting of cetyl pyridinium chloride, polyphenols, phenolic compounds, stannous ions, zinc ions, and the like.

Examples of antibacterial phenolic compounds, including both synthesized and natural-based phenolic compounds, include 4-allylcatechol, p-hydroxybenzoic acid esters including benzylparaben, butylparaben, ethylparaben, methylparaben and propylparaben, 2-benzylphenol, butylated hydroxyanisole, butylated hydroxytoluene, capsaicin, carvacrol, creosol, eugenol, guaiacol, halogenated bisphenolics including hexachlorophene and bromochlorophene, 4-hexylresorcinol, 8-hydroxyquinoline and salts thereof, salicylic acid esters including menthyl salicylate, methyl salicylate and phenyl salicylate, phenol, pyrocatechol, salicylanilide, thymol, Triclosan (2',4,4'-trichloro-2-hydroxy-diphenyl ether) and Triclosan monophosphate.

Other suitable antibacterial agents include, without limitation, copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, sulfonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metronidazole, neomycin, kanamycin and clindamycin, and the like. A further illustrative list of useful antibacterial agents is provided in U.S. Pat. No. 5,776,435. If present, these additional antimicrobial agents are present in an antimicrobial effective total amount, typically 0.05% to 10%, for example 0.1% to 3% by weight, of the composition.

The compositions described herein may be formulated with optional other ingredients, including without limitation, anticaries agents, anticalculus or tartar control agents, anionic carboxylate polymers, viscosity modifiers, surfactants, flavorants, pigments, signals (flavor, color, light, heat, smell and other signals that signal the efficacious or advantageous use of the composition), and the like.

As an anticaries agent, one or more fluoride-releasing salts are optionally present in an amount providing a total of 100 to 20,000 ppm, 200 to 5,000 ppm, or 500 to 2,500 ppm, fluoride ions. Where sodium fluoride is the sole fluoride-releasing salt present, illustratively an amount of 0.01% to 5%, 0.05% to 1% or 0.1% to 0.5%, sodium fluoride by weight can be present in the composition. Other anticaries agents can be used, such as arginine and arginine derivatives (e.g., ethyl lauroyl arginine (ELAH)).

In various embodiments, the compositions comprise an orally acceptable source of fluoride ions, which serves as an anticaries agent. One or more such sources can be present. Suitable sources of fluoride ions include fluoride, monofluorophosphate and fluorosilicate salts as well as amine fluorides, including olaflur (N'-octadecyltrimethylendiamine-N, N,N'-tris(2-ethanol)-dihydrofluoride).

In another embodiment the composition comprises an orally acceptable anticalculus agent. One or more such agents can be present. Suitable anticalculus agents include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts illustratively include monobasic, dibasic and tribasic sodium phosphates, sodium tripolyphosphate, tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include anionic polycarboxylate polymers. The anionic polycarboxylate polymers contain carboxyl groups on a carbon backbone and include polymers or copolymers of acrylic acid, methacrylic, and maleic anhydride. Non-limiting examples include polyvinyl methyl ether/maleic anhydride (PVME/MA) copolymers, such as those available under the Gantrez brand from ISP, Wayne, N.J. Still other useful anticalculus agents include sequestering agents including hydroxycarboxylic acids such as citric, fumaric, malic, glutaric and oxalic acids and salts thereof, and aminopolycarboxylic acids such as ethylenediaminetetraacetic acid (EDTA). One or more anticalculus agents are optionally present in the composition in an anticalculus effective total amount, typically 0.01% to 50%, for example 0.05% to 25% or 0.1% to 15% by weight.

In various embodiments, the anticalculus system comprises a mixture of sodium tripolyphosphate (STPP) and a tetrasodium pyrophosphate (TSPP). In various embodiments, the ratio of TSPP to STPP ranges 1:2 to 1:4. In a preferred embodiment, the first anticalculus active ingredient, TSPP is present at 1 to 10% and the second anticalculus active ingredient, STPP is present at 1 to 10%.

In one embodiment, the anionic polycarboxylate polymer is present 0.1% to 5%. In another embodiment, the anionic polycarboxylate polymer is present 0.5% to 1.5%, most preferably at 1% of the oral care composition. In one embodiment according to the present invention, the anticalculus system comprises a copolymer of maleic anhydride and methyl vinyl ether.

In various embodiments, the ratio of TSPP to STPP to the synthetic anionic polycarboxylate ranges 5:10:1 to 5:20:10 (or 1:4:2). In one embodiment, the anticalculus system of the oral care composition comprises TSPP, STPP, and a polycarboxylate such as a copolymer of maleic anhydride and methyl vinyl ether at a ratio of 1:7:1. In a non-limiting embodiment, the anticalculus system consists essentially of TSPP present at 0.5% to 10%, STPP present at 1% to 10%, and a copolymer of maleic anhydride and methyl vinyl ether present at 0.5% to 1.5%.

In another embodiment the composition comprises an orally acceptable stannous ion source useful, for example, in helping reduce gingivitis, plaque, calculus, caries or sensitivity. One or more such sources can be present. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of 0.01% to 10%, for example 0.1% to 7% or 1% to 5% by weight of the composition.

In another embodiment the composition comprises an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of 0.05% to 3%, for example 0.1% to 1%, by weight of the composition.

In another embodiment the composition comprises an orally acceptable breath-freshening agent. One or more such agents can be present in a breath-freshening effective total amount. Suitable breath-freshening agents include without limitation zinc salts such as zinc gluconate, zinc citrate and zinc chlorite, .alpha.-ionone and the like.

In another embodiment the composition comprises an orally acceptable antiplaque, including plaque disrupting, agent. One or more such agents can be present in an antiplaque effective total amount. Suitable antiplaque agents include without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

Among useful carriers for optional inclusion in a composition of the invention are diluents, abrasives, bicarbonate salts, pH modifying agents, surfactants, foam modulators, thickening agents, viscosity modifiers, humectants, sweeteners, flavorants and colorants. One carrier material, or more than one carrier material of the same or different classes, can optionally be present. Carriers should be selected for compatibility with each other and with other ingredients of the composition.

In one embodiment a composition of the invention comprises at least one abrasive, useful for example as a polishing agent. Any orally acceptable abrasive can be used, but type, fineness (particle size) and amount of abrasive should be selected so that tooth enamel is not excessively abraded in normal use of the composition. Suitable abrasives include without limitation silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. One or more abrasives are optionally present in an abrasive effective total amount, typically 5% to 70%, for example 10% to 50% or 15% to 30% by weight of the composition. Average particle size of an abrasive, if present, is generally 0.1 to 30 μm, for example 1 to 20 μm or 5 to 15 μm.

In a further embodiment a composition of the invention comprises at least one bicarbonate salt, useful for example to impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate and the like. One or more bicarbonate salts are optionally present in a total amount of 0.1% to 50%, for example 1% to 20% by weight of the composition.

In a still further embodiment a composition of the invention comprises at least one pH modifying agent. Such agents include acidifying agents to lower pH, basifying agents to raise pH and buffering agents to control pH within a desired range. For example, one or more compounds selected from acidifying, basifying and buffering agents can be included to provide a pH of 2 to 10, or in various illustrative embodiments 2 to 8, 3 to 9, 4 to 8, 5 to 7, 6 to 10, 7 to 9, etc. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

In a still further embodiment a composition of the invention comprises at least one surfactant, useful for example to compatibilize other components of the composition and thereby provide enhanced stability, to help in cleaning the dental surface through detergency, and to provide foam upon agitation, e.g., during brushing with a dentifrice composition of the invention. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of 0.01% to 10%, for example 0.05% to 5% or 0.1% to 2% by weight of the composition.

In a still further embodiment a composition of the invention comprises at least one foam modulator, useful for example to increase amount, thickness or stability of foam generated by the composition upon agitation. Any orally acceptable foam modulator can be used, including without limitation polyethylene glycols (PEGs), also known as polyoxyethylenes. High molecular weight PEGs are suitable, including those having an average molecular weight of 200,000 to 7,000,000, for example 500,000 to 5,000,000 or 1,000,000 to 2,500,000. One or more PEGs are optionally present in a total amount of 0.1% to 10%, for example 0.2% to 5% or 0.25% to 2% by weight of the composition.

In a still further embodiment a composition of the invention comprises at least one thickening agent, useful for example to impart a desired consistency and/or mouth feel to the composition. Any orally acceptable thickening agent can be used, including without limitation carbomers, also known as carboxyvinyl polymers, carrageenans, also known as Irish moss and more particularly t-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. One or more thickening agents are optionally present in a total amount of 0.01% to 15%, for example 0.1% to 10% or 0.2% to 5% by weight of the composition.

In a still further embodiment a composition of the invention comprises at least one viscosity modifier, useful for example to inhibit settling or separation of ingredients or to promote redispersibility upon agitation of a liquid composition. Any orally acceptable viscosity modifier can be used, including without limitation mineral oil, petrolatum, clays and organomodified clays, silica and the like. One or more viscosity modifiers are optionally present in a total amount of 0.01% to 10%, for example 0.1% to 5% by weight of the composition.

In a still further embodiment a composition of the invention comprises at least one humectant, useful for example to prevent hardening of a toothpaste upon exposure to air. Any orally acceptable humectant can be used, including without limitation polyhydric alcohols such as glycerin, sorbitol, xylitol or low molecular weight PEGs. Most humectants also function as sweeteners. One or more humectants are optionally present in a total amount of 1% to 70%, for example 1% to 50%, 2% to 25%, or 5% to 15% by weight of the composition.

In a still further embodiment a composition of the invention comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.005% to 5% by weight of the composition.

In one embodiment, a composition of the invention comprises at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, .alpha.-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of 0.01% to 5%, for example 0.1% to 2.5% by weight of the composition.

In one embodiment, a composition of the invention comprises at least one colorant. Colorants herein include pigments, dyes, lakes and agents imparting a particular luster or reflectivity such as pearling agents. A colorant can serve a number of functions, including for example to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of 0.001% to 20%, for example 0.01% to 10% or 0.1% to 5% by weight of the composition.

The present invention is further illustrated, but not limited by, the following examples.

EXAMPLES

Example 1: A Toothpaste Formulation of the Present Invention

A toothpaste formulation is prepared using the following ingredients:

| Ingredient | Percentage of Formulation |
| --- | --- |
| Water (Deionized) | 32.09 |
| Sorbitol (70% Soln) | 22 |
| Glycerin | 13 |
| Xylitol | |
| Propylene Glycol | 3 |
| CMC 500T | 0.8 |
| Xanthan | 0.4 |
| Carageenan | |
| TiO2 | 0.3 |
| TSPP | 0.5 |
| NaF | |
| NaMFP | 0.76 |
| Sodium Saccharin | 0.3 |
| Silica (Regular) | 5 |
| High Cleaning Silica (HCS) | 15 |
| Silica Thickener | 2.75 |
| Zinc Oxide | 1 |
| Sodium Bicarbonate | |
| SLS | 1.5 |
| Flavor | 1.2 |
| Extract | 0.4 |
| | 67.91 |

Example 2: An Alternate Toothpaste Formulation of the Present Invention

A toothpaste formulation is prepared using the following ingredients:

| Ingredient | Percentage of Formulation |
|---|---|
| Water (Deionized) | 31.99 |
| Sorbitol (70% Soln) | 24 |
| Glycerin | 14 |
| Xylitol | |
| Propylene Glycol | |
| CMC 500T | 0.8 |
| Xanthan | 0.4 |
| Carageenan | |
| TiO2 | 0.3 |
| TSPP | 0.5 |
| NaF | |
| NaMFP | 0.76 |
| Sodium Saccharin | 0.3 |
| Silica (Regular) | 5 |
| High Cleaning Silica (HCS) | 15 |
| Silica Thickener | 2.75 |
| Zinc Oxide | 1 |
| Sodium Bicarbonate | |
| SLS | 1.5 |
| Flavor | 1.2 |
| Extract | 0.5 |
| | 68.01 |

Example 3: An Alternate Toothpaste Formulation of the Present Invention

A toothpaste formulation is prepared using the following ingredients:

| Ingredient | Percentage of Formulation |
|---|---|
| Water (Deionized) | 35.357 |
| Sorbitol (70% Soln) | 17 |
| Glycerin | 20 |
| Xylitol | |
| Propylene Glycol | |
| CMC 500T | 0.8 |
| Xanthan | 0.3 |
| Carageenan | |
| TiO2 | 0.3 |
| TSPP | |
| NaF | 0.243 |
| NaMFP | |
| Sodium Saccharin | 0.3 |
| Silica (Regular) | 10 |
| High Cleaning Silica (HCS) | 10 |
| Silica Thickener | 2.5 |
| Zinc Oxide | |
| Sodium Bicarbonate | |
| SLS | 1.5 |
| Flavor | 1.2 |
| Extract | 0.5 |
| | 100 |

Example 4: An Alternate Toothpaste Formulation of the Present Invention

A toothpaste formulation is prepared using the following ingredients:

| Ingredient | Percentage of Formulation |
|---|---|
| Water (Deionized) | 30.19 |
| Sorbitol (70% Soln) | 17 |
| Glycerin | 20 |
| Xylitol | 1.8 |
| Propylene Glycol | |
| CMC 500T | 0.8 |
| Xanthan | 0.3 |
| Carageenan | |
| TiO2 | 0.3 |
| TSPP | 0.5 |
| NaF | |
| NaMFP | 0.76 |
| Sodium Saccharin | 0.3 |
| Silica (Regular) | 10 |
| High Cleaning Silica (HCS) | 10 |
| Silica Thickener | 2.25 |
| Zinc Oxide | 1 |
| Sodium Bicarbonate | 1.6 |
| SLS | 1.5 |
| Flavor | 1.2 |
| Extract | 0.5 |
| | 100 |

Example 5: An Alternate Toothpaste Formulation of the Present Invention

A toothpaste formulation is prepared using the following ingredients:

| Ingredient | Percentage of Formulation |
|---|---|
| Water (Deionized) | 32.29 |
| Sorbitol (70% Soln) | 17 |
| Glycerin | 18 |
| Xylitol | |
| Propylene Glycol | |
| CMC 500T | 0.8 |
| Xanthan | 0.3 |
| Carageenan | |
| TiO2 | 0.3 |
| TSPP | 0.5 |
| NaF | |
| NaMFP | 0.76 |
| Sodium Saccharin | 0.3 |
| Silica (Regular) | 14 |
| High Cleaning Silica (HCS) | 6 |
| Silica Thickener | 2 |
| Zinc Oxide | 1 |
| Sodium Bicarbonate | 4 |
| SLS | 1.5 |
| Flavor | 1.2 |
| Extract | 0.05 |
| | 100 |

Example 6: A Toothpaste Formulation of the Present Invention

A toothpaste formulation is prepared using the following ingredients:

| Ingredient | Percentage of Formulation |
|---|---|
| Water | 29.257 |
| Sorbitol | 17 |
| Glycerin | 20 |
| Propylene Glycol | 3 |
| Xylitol | 3 |
| CMC 500T | 0.6 |
| Xanthan | 0.4 |
| TSPP | |
| NaMFP | |
| NaF | 0.243 |
| High Cleaning Silica | 15 |
| Regular Silica | 5 |
| Silica Thickening | 3 |
| Carbopol | |
| Sodium Saccharin | 0.3 |
| Calcium Carbonate | |
| Alumina | |
| Sodium Silicate | |
| Zinc Oxide | |
| Sodium Bicarbonate | |
| SLS | 1.5 |
| Flavor | 1.2 |
| Black seed oil | 0.5 |
| Moring extract | |
| | 100 |

Example 7: A Toothpaste Formulation of the Present Invention

A toothpaste formulation is prepared using the following ingredients:

| Ingredient | Percentage of Formulation |
|---|---|
| Water | 29.94 |
| Sorbitol | 17 |
| Glycerin | 20 |
| Propylene Glycol | 3 |
| Xylitol | 1.5 |
| CMC 500T | 0.4 |
| Xanthan | 0.2 |
| TSPP | 0.5 |
| NaMFP | 0.76 |
| NaF | |
| High Cleaning Silica | 15 |
| Regular Silica | 5 |
| Silica Thickening | 2 |
| Carbopol | 0.2 |
| Sodium Saccharin | 0.3 |
| Calcium Carbonate | |
| Alumina | |
| Sodium Silicate | |
| Zinc Oxide | 1 |
| Sodium Bicarbonate | |
| SLS | 1.5 |
| Flavor | 1.2 |
| Black seed oil | 0.5 |
| Moring extract | |
| | 100 |

Example 8: A Toothpaste Formulation of the Present Invention

A toothpaste formulation is prepared using the following ingredients:

| Ingredient | Percentage of Formulation |
|---|---|
| Water | 24.24 |
| Sorbitol | 5 |
| Glycerin | 10 |
| Propylene Glycol | |
| Xylitol | 10 |
| CMC 500T | 0.8 |
| Xanthan | 0.3 |
| TSPP | 0.5 |
| NaMFP | 0.76 |
| NaF | 0 |
| High Cleaning Silica | |
| Regular Silica | |
| Silica Thickening | |
| Carbopol | |
| Sodium Saccharin | 0.2 |
| Calcium Carbonate | 33 |
| Alumina | 10 |
| Sodium Silicate | 1 |
| Zinc Oxide | 1 |
| Sodium Bicarbonate | |
| SLS | 1.5 |
| Flavor | 1.2 |
| Black seed oil | 0.3 |
| Moring extract | 0.2 |
| | 100 |

Example 9: A Toothpaste Formulation of the Present Invention

A toothpaste formulation is prepared using the following ingredients:

| Ingredient | Percentage of Formulation |
|---|---|
| Water | 24.54 |
| Sorbitol | 0 |
| Glycerin | 10 |
| Propylene Glycol | |
| Xylitol | 35 |
| CMC 500T | 1 |
| Xanthan | |
| TSPP | 0.5 |
| NaMFP | 0.76 |
| NaF | 0 |
| High Cleaning Silica | |
| Regular Silica | |
| Silica Thickening | |
| Carbopol | |
| Sodium Saccharin | 0 |
| Calcium Carbonate | 25 |
| Alumina | |
| Sodium Silicate | 1 |
| Zinc Oxide | 2 |
| Sodium Bicarbonate | 7 |
| SLS | 1.5 |
| Flavor | 1.2 |
| Black seed oil | 0.4 |
| Moring extract | 0.1 |
| | 100 |

Example 10: Analysis of the Concentration of Soluble Zinc in the Formulations of the Present Invention Zinc is known to have antimicrobial and antibacterial benefits. Extracts of *Nigella sativa*, or oils obtained from *Nigella sativa* are know to have antimicrobial and antibacterial benefits. Formulations of the present invention will be analyzed, using standard analytical techniques, such as, for example, mass spectrometry, and the like, to determine the concentration of soluble zinc in the formulations. The levels of soluble zinc in formulations of the present invention will be compared to formulations lacking extracts of *Nigella sativa*, or oils obtained from *Nigella sativa*, to determine if the antimicrobial and antibacterial properties of the formulations of the present invention may be attributed to the effect of *Nigella sativa*, or oils obtained from *Nigella sativa* on the concentration od soluble zinc in the formulation.

Example 11: In Vitro Assay of the Antimicrobial Properties of *Nigella sativa*

The antimicrobial properties of *Nigella sativa* were investigated using a standard microbiological assay. Briefly, tryptic soy agar plates were prepared and the test micro-organisms listed in the table below were grown in tryptic soy broth (at 35° C. for 24-48 hrs). Samples of the test micro-organisms were spread onto individual test plates, and 10 and 25 µl of neat *Nigella sativa* oil at was spotted onto the plates and the zone of inhibition was measured (corresponding to the ability of the *Nigella sativa* oil to kill or arrest the growth of the test micro-organism) at [TIME]. The size of the zone of inhibition is partly influenced by the water solubility and amount of test compound (and % or concentration) applied to the petri plates.

| Micro-organism | Zone of Inhibition |
| --- | --- |
| *Eschericia. coli* #8739 | 0.133 mm |
| *Staphylococcus. aureus* # 6538 | 23.33 mm and 23.25 mm |
| *Listeria monocytogenes* #751 | 13.33 mm |
| *Candida albicans* #10231 | 0.300 mm and 3.35 mm |
| *Actinomyces viridans* #11563 | 2.50 mm and 20.0 mm and 8.4 mm and 8.7 mm |
| *Aspergillus brasiliensis* #16404 | 0.10 mm |
| *Citrobacter fruendii* #8090 | 0.10 mm |
| *Staphylococcus epidermidis* #12228 | 7.7 mm and 9.0 mm |

*Nigella sativa* is very effective against Gram positive organisms. These are the predominant bacteria in the oral cavity and on the teeth and gums. *Nigella sativa* is an effective natural antimicrobial providing bacteriostasis and bacteriocidal activity against bacteria, which cause caries, bad breath, gum disease and other oral infections. For subsequent testing, *Actinomyces viridans*, a common microbe of the mouth that is easy to grow and subculture in anaerobic conditions was used.

Example 12: In Vitro Assay of the Ability of the Formulations of the Present Invention to Kill *Actinomyces viridans*

A standard microbiological suspension time kill test was performed using routine microbiological techniques. 50% solutions of a toothpaste formulation containing *Nigella sativa* was prepared and tested. A control toothpaste formulation that did not contain *Nigella sativa* was also prepared. Test samples of *Actinomyces viridans* were grown in Brain Heart Infusion broth and test agar plates were prepared. The toothpaste formulations were inoculated and after 30 seconds of mixing, recovery was performed and the surviving organisms were compared to the inoculum control (sterile di water).

Inoculum was 6.2 log. The control toothpaste formulation showed a 2.6 log reduction. The toothpaste formulation containing *Nigella sativa* showed a 3.2 log reduction, corresponding to a 99.93% reduction.

Example 13: Microbiological Robustness Testing of the Formulations of the Present Invention

*Nigella sativa* has some effectiveness against all organisms tested, thus useful in a dentifrice product giving the product added robustness for product manufacturing safety, extended shelf life and consumer safety. Formula robustness is measure by short term pool inoculated studies (microbiological robustness Testing—MRT) and preservative screening tests (preservative effectiveness tests—PET). The toothpaste formulations below were tested. Formulations A and B were toothpaste formulations (control and containing *Nigella sativa* oil, respectively). Formulations C and D were gel toothpaste formulations (control and containing *Nigella sativa* oil, respectively).

| Ingredient | Formulation A | Formulation B | Formulation C | Formulation D |
| --- | --- | --- | --- | --- |
| Water (Deionized) | 40.86 | 39.86 | 33.36 | 32.86 |
| Sorbitol (70% Soln) | 15 | 15 | 17 | 17 |
| Glycerin | 15 | 15 | 20 | 20 |
| CMC | 1 | 1 | 1 | 1 |
| Xanthan | 0.3 | 0.3 | 0.3 | 0.3 |
| $TiO_2$ | 0.3 | 0.3 | 0 | 0 |
| TSPP | 0.5 | 0.5 | 0.5 | 0.5 |
| NaF | 0.243 | 0.243 | 0.243 | 0.243 |
| Sodium Saccharin | 0.3 | 0.3 | 0.3 | 0.3 |
| Silica (Regular) | 5 | 5 | 10 | 10 |
| High Cleaning Silica (HCS) | 15 | 15 | 10 | 10 |
| Silica Thickener | 2.5 | 2.5 | 3.5 | 3.5 |
| Zinc Oxide | 1 | 1 | 0.5 | 0.5 |
| Zinc Gluconate | 0.3 | 0.3 | 0.6 | 0.6 |
| SLS | 1.5 | 1.5 | 1.5 | 1.5 |
| Flavor | 1.2 | 1.2 | 1.2 | 1.2 |
| Color | 0 | 0 | 0.0001 | 0.0001 |
| *Nigella sativa* oil | 0 | 1 | 0 | 0.5 |
| Total (%) | 100 | 100 | 100 | 100 |

Study 1: Bacteria pool=*Pseudomonas aeruginosa* #9027, *Escherisia coli* #8739, *Staphylococcus aureus* #6538.

Yeast and Mold pool=*Aspergillus brasiliensis* #16404 and *Candida Albicans* #10231.

Results: MRT data 1 hour recovery—Bacteria pool:

Water control (inoculum)=6.8 log. Formulation A showed a 3.0 log reduction, whilst Formulation B containing showed a 4.7 log reduction. Formulation C showed a 3.1 log reduction, and Formulation C showed a 4.8 log reduction.

Study 2: Formulations B and D were inoculated according to the tables shown below and analyzed for antimicrobial effectiveness on weeks 2, and week 4 post inoculation.

| Formulation B | ANTIMICROBIAL EFFECTIVNESS/ROBUSTNESS TEST | | |
|---|---|---|---|
| Organism | Initial | Week 2 | Week 4 |
| S. aurues | $1.1 \times 10^5$ | <10 cfu/g | <10 cfu/g |
| P. aeruginosa | $8.8 \times 10^5$ | <10 cfu/g | <10 cfu/g |
| E. coli | $8.7 \times 10^5$ | <10 cfu/g | <10 cfu/g |
| C. Albicans | $1.5 \times 10^5$ | <10 cfu/g | <10 cfu/g |
| A Niger | $5.0 \times 10^5$ | <10 cfu/g | <10 cfu/g |

| Formulation D | ANTIMICROBIAL EFFECTIVNESS/ROBUSTNESS TEST | | |
|---|---|---|---|
| Organism | Initial | Week 2 | Week 4 |
| S. aurues | $1.1 \times 10^5$ | <10 cfu/g | <10 cfu/g |
| P. aeruginosa | $8.8 \times 10^5$ | <10 cfu/g | <10 cfu/g |
| E. coli | $8.7 \times 10^5$ | <10 cfu/g | <10 cfu/g |
| C. Albicans | $1.5 \times 10^5$ | <10 cfu/g | <10 cfu/g |
| A Niger | $5.0 \times 10^5$ | <10 cfu/g | <10 cfu/g |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A composition,
   wherein the composition is formulated as a toothpaste, and the composition comprises:
   a. black seed oil at an amount from 0.3 wt % to 1 wt % of the composition;
   b. a mixture of zinc oxide and zinc citrate at an amount from 0.3 wt % to 1.0 wt % of the composition;
   c. at least one abrasive material at an amount from 1 wt % to 70 wt % of the composition; and
   d. a humectant;
   wherein the composition reduces the growth of microbial populations by at least 4 log units in a microbiological robustness assay.

* * * * *